United States Patent [19]

Gruber

[11] 4,385,159
[45] May 24, 1983

[54] DIMETHACRYLIC ACID ESTERS OF DIEMETHYLOLTETRAHYDROFURAN AND ITS DERIVATIVES, THEIR PREPARATION AND APPLICATION AS ADHESIVES

[75] Inventor: Werner Gruber, Düsseldorf, Fed. Rep. of Germany

[73] Assignee: Henkel Kommanditgesellschaft Auf Aktien, Düsseldorf-Holthausen, Fed. Rep. of Germany

[21] Appl. No.: 355,128

[22] Filed: Mar. 5, 1982

Related U.S. Application Data

[62] Division of Ser. No. 269,894, Jun. 3, 1981, Pat. No. 4,341,711.

[30] Foreign Application Priority Data

Jun. 12, 1980 [DE] Fed. Rep. of Germany ....... 3021941

[51] Int. Cl.$^3$ .................. C08F 24/00; C08F 34/02
[52] U.S. Cl. .................... 526/270; 524/549
[58] Field of Search ........................... 526/270

[56] References Cited

U.S. PATENT DOCUMENTS 3,479,246 11/1969 Stapleton ........................ 526/270
3,634,737 1/1972 Stapleton ........................ 260/86.1
3,923,737 12/1975 George et al. ................... 260/47

FOREIGN PATENT DOCUMENTS 2202040 7/1973 Fed. Rep. of Germany .

Primary Examiner—Harry Wong, Jr.
Attorney, Agent, or Firm—Hammond & Littell, Weissenberger and Muserlian

[57] ABSTRACT

The present invention relates to dimethacrylic acid esters of dimethyloltetrahydrofuran and its derivatives having the formula:

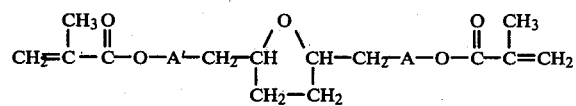

wherein A and A' individually have the formula:

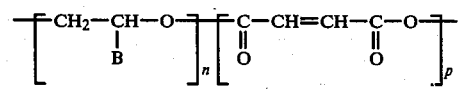

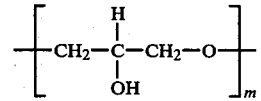

wherein B is a member selected from the group consisting of $CH_3$ and H, n is an integer from 0 to 5, m is 0 or 1, and p is 0 or 1; their process of preparation and their use as adhesive components of anaerobic adhesive compositions.

11 Claims, No Drawings

DIMETHACRYLIC ACID ESTERS OF DIEMETHYLOLTETRAHYDROFURAN AND ITS DERIVATIVES, THEIR PREPARATION AND APPLICATION AS ADHESIVES

This is a division of Ser. No. 269,894, filed June 3, 1981, now U.S. Pat. No. 4,341,711.

BACKGROUND OF THE INVENTION

The present invention concerns new dimethacrylic acid esters derived from 2,5-dimethyloltetrahydrofuran and its derivatives. It also concerns the preparation of such compounds as well as their use as adhesives, particularly as solvent-free adhesives that harden spontaneously as oxygen is excluded.

Methacrylic acid esters, both the monoesters as well as the diesters, have been known for a long time and can be used, among other uses, as an adhesive component for adhesives that harden spontaneously under the exclusion of oxygen. For example, dimethacrylates of propoxylated diphenylolpropane as well as special derivatives of tricyclodecane have been used for this purpose.

With reference to their application, however, anaerobically hardening adhesives based on these dimethacrylates leave something to be desired with respect to greater adhesive strength. Tetrahydrofurfuryl methacrylate is a monomer that can be used for the preparation of anaerobically hardening adhesives with high strength at room temperature, but a strongly annoying odor is observed due to its relatively high volatility. In addition, the resistance to heat is extremely unfavorable because of the low ceiling temperature of the polymer formed.

OBJECTS OF THE INVENTION

An object of the present invention is the development of new, technically more valuable dimethacrylates that contribute, on the basis of their constitution and characteristics, an improvement with respect to the known state of the art.

Another object of the present invention is the development of dimethacrylic acid esters of dimethyloltetrahydrofuran and its derivatives having the formula:

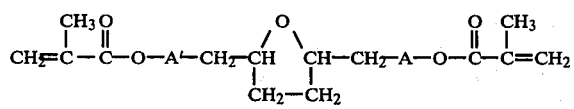

wherein A and A' individually have the formula:

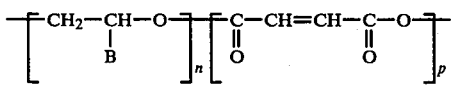

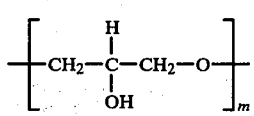

wherein B is a member selected from the group consisting of $CH_3$ and H, n is an integer from 0 to 5, m is 0 or 1, and p is 0 or 1.

A further object of the present invention is the development of a process for the production of the above dimethacrylic acid esters.

A yet further object of the present invention is the development of an adhesive composition hardenable under exclusion of oxygen utilizing the above dimethacrylic acid esters.

These and other objects of the present invention will become more apparent as the description thereof proceeds.

DESCRIPTION OF THE INVENTION

The subject of the invention are dimethacrylates of the general formula:

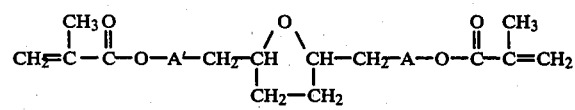

in which A or A' has the following significance:

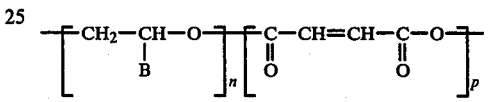

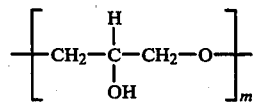

with $B=CH_3$ or H, and n, p and m representing whole numbers that may assume the values: $n=0$ to 5, and $m=0$ or 1, and $p=0$ or 1.

More particularly, the present invention relates to dimethacrylic acid esters of dimethyloltetrahydrofuran and its derivatives having the formula:

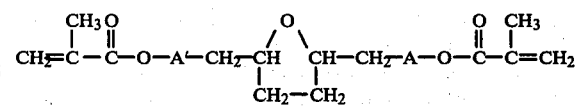

wherein A and A' individually have the formula:

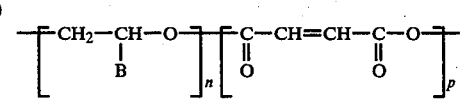

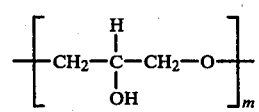

wherein B is a member selected from the group consisting of $CH_3$ and H, n is an integer from 0 to 5, m is 0 to 1, and p is 0 or 1.

For the simple case, where $B=H$, and n, m and $p=0$, the dimethacrylate of 2,5-dimethyloltetrahydrofuran (Compound A) is present. However, when $n=1$, m and $p=0$ and $B=H$, the following Compound B is obtained:

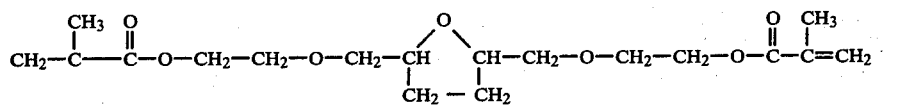

Choosing n=0, m=1 and p=1, the following Compound C is obtained:

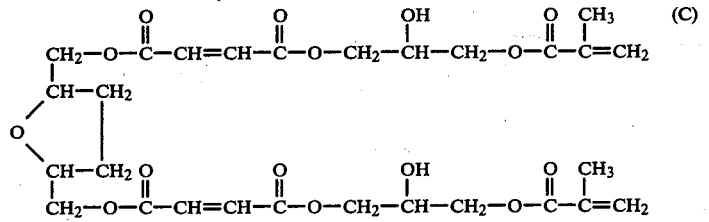

When n=1, B=H, m=1 and p=1, the following Compound D is obtained:

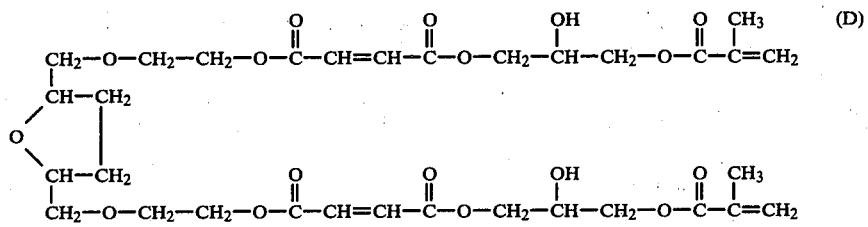

The dimethacrylates according to the invention are prepared by well known reactions. For example, 2,5-dimethyloltetrahydrofuran can be reacted with methacrylic acid or its chloride or methyl ester to give Compound A. It is also possible to alkoxylate 2,5-dimethyloltetrahydrofuran with ethylene oxide and/or propylene oxide and then react with methacrylic acid or its chloride or methyl ester to give Compound B.

Furthermore, the dimethacrylates according to the invention can be prepared by converting 1 mol of 2,5-dimethyloltetrahydrofuran with 1 to 2 mols of maleic acid anhydride in a well known manner and then reacting with 2 mols of glycidyl methacrylate to give Compound C. Finally, a variation of the preparation consists of alkoxylating 2,5-dimethyloltetrahydrofuran first with 1 to 10, especially 2 to 4, mols of ethylene oxide and/or propylene oxide and then forming the ester with maleic acid anhydride and lastly reacting with glycidyl methacrylate to give Compound D. Suitable catalysts such as quaternary ammonium compounds can be used for the acceleration of the addition reaction with alkylene oxide or propylene oxide.

The suitable starting material for the preparation of the compounds according to the invention is commercial 2,5-dimethyloltetrahydrofuran. The reactions can be performed without solvents at 80° to 120° C., if desired under a protective gas or in an inert solvent, for example, chlorinated hydrocarbons. The compounds obtained by this method are highly viscous substances. Technically very suitable compounds still may have a low acid number of up to approximately 12.

The compounds according to the invention are used as a significant constituent of adhesives or sealing materials that harden under the exclusion of oxygen in amounts of from about 10% by weight to about 98.5% by weight of the adhesive. However, these mixtures also may contain additional methacrylates. Suitable additional methacrylates, for example, are difunctional methacrylates, such as ethylene glycol dimethacrylate, triethylene glycol dimethacrylate, polyethylene glycol dimethacrylate, hydroxyethyl methacrylate, hydroxypropyl methacrylate, dimethacrylate of dimethyloltricyclodecane, or monofunctional methacrylates, such as ethylhexyl methacrylate, cyclohexyl methacrylate, 5,6-dihydrodicyclopentadienyl methacrylate, tetrahydrofurfuryl methacrylate.

Another important constituent of the anaerobically hardening systems are the peroxide initiators. These are mainly hydroperoxides that are derived from hydrocarbons with a chain length or carbon content of 3 to 18 carbon atoms. Suitable, for example, are cumene hydroperoxide, tert-butyl hydroperoxide, methylethyl ketone hydroperoxide, diisopropylbenzene hydroperoxide.

Also suitable are those peroxides that have a half-life of 10 hours at a temperature between about 80° and 140° C. Here, tert-butyl perbenzoate, di-tert-butyl diperoxyphthalate, 2,5-dimethyl-2,2-bis-(tert-butylperoxy)-hexane, bis-(1-hydroxycyclohexyl)-peroxide, tert-butyl peroxyacetate, 2,5-dimethylhexyl-2,5-di-(peroxybenzoate), tert-butyl valerate, 2,2-bis-(tert-butylperoxy)-butane and di-tert-butylperoxide are suitable.

The peroxide initiators shall be present in an amount of 0.1% to 20%, particularly 1.0% to 10%, based on the total mixture. Usually they are used in the form of stabilized solutions or pastes, that means with a relatively low content of inert substances, such as dimethyl phthalate or cumene.

In addition, an organic amine may be used as an accelerator, such as substituted hydrazides like p-toluenesulfonic acid hydrazide, or benzoic acid sulfinimide or amines like N,N-dimethyl-p-toluidine and tri-n-butylamine. Amines shall be used in very small amounts of 0.1% to 2.5% by weight only.

Stabilizers are added to advantage to these adhesives and sealing agents. Suitable as stabilizers are quinone or hydroquinone in concentrations of 100 to 1,000 ppm, preferably 200 to 500 ppm, based on the components that can be polymerized. Accelerator and stabilizer must be added in mutually adjusted ratios to obtain optimal characteristics for the adhesives or sealing agents. Usually they are added in amounts of 0.1% to 3% by weight, based on polymerizable components.

For certain applications, these adhesives or sealing materials may contain additions of plasticizers, thickening agents or pigments. The adhesives or sealing agents are prepared by a mixing process of all components at room temperature, and they are stable for years in most cases, provided that they are stored in containers permeable by air, such as polyethylene bottles. When the adhesives or sealing agents are applied between metal surfaces, they polymerize quickly under exclusion of oxygen with the formation of a solid bond between the surfaces. The advantages of the adhesives or sealing agents obtainable according to the invention may be seen, among others, in the fact that the parts to be joined can be glued together at room temperature and that stress can be placed on them after only a short time. Furthermore, aluminum or aluminum alloys also can be glued with adequate strength in addition to iron alloys. The heat resistance of the adhesive bonding is excellent.

The obtainable adhesive of the invention is suitable for the bonding of metals especially when the glued joint must have great strength with good heat resistance. Consequently the adhesives are used technically for the glueing of sheet metals or metal parts of different materials, for the attaching of bearing shafts, for the sealing of pipe joints and other similar applications. The relatively small decrease in strength at 100° to 150° C. is noteworthy. Considerable torque moments can still be measured even at 180° C.

The following examples are illustrative of the practice of the invention without being limitative thereto.

EXAMPLE 1

Dimethacrylate of 2,5-Dimethyloltetrahydrofuran

Compound A 2,5-Dimethyloltetrahydrofuran in an amount of 132 gm (1 mol) was dissolved in 400 ml of anhydrous tetrahydrofuran and mixed with 202 gm (2 mols) of triethylamine. Within two hours, 208 gm (2 mols) of methacrylic acid chloride were added dropwise at 5° C., with agitation and cooling. Then the temperature was maintained at 20° C. for one hour and at 50° C. for one hour. The triethylamine hydrochloride was removed by suction filtering and the solvent was removed under vacuum. The residue was taken up in ethyl acetate and washed with water and sodium bicarbonate solution. After drying over sodium sulfate, the solvent was evaporated. A highly viscous, colorless oil remained.

Yield: 204 gm=76%
Analysis: $C_{14}H_{20}O_5$ (MW 268.31), Calc.: C 62.67%, H 7.51%, Found: C 62.3%, H 7.32%.

The dimethacrylate of 2,5-dimethyloltetrahydrofuran was also prepared by direct esterification with methacrylic acid in carbon tetrachloride as solvent and by reesterification with an excess of methyl methacrylate.

EXAMPLE 2

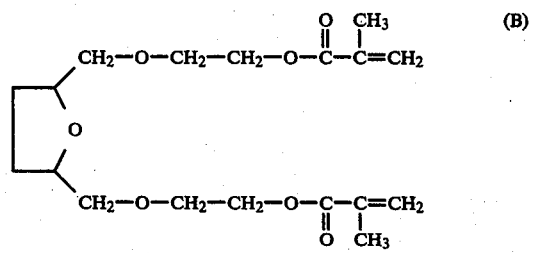

Ethoxylated 2,5-dimethyloltetrahydrofuran (OH number=409.25) in the amount of 110 gm (0.5 mol) was dissolved in 300 ml tetrahydrofuran and mixed with 101 gm (1 mol) of triethylamine. With agitation and cooling, 104 gm (1 mol) of methacrylic acid chloride were added dropwise at 5° C. The subsequent reaction and working up were carried out as described in Example 1.

The obtained dimethyacrylate is a highly viscous, colorless oil.

Yield: 152 gm=80% of theoretical
Analysis: $C_{18}H_{28}O_7$ (MW 356.42), Calc.: C 60.66%, H 7.92%, Found: C 59.3%, H 7.94%.

Alternatively, the dimethacrylate was prepared by direct esterification with methacrylic acid in carbon tetrachloride.

EXAMPLE 3

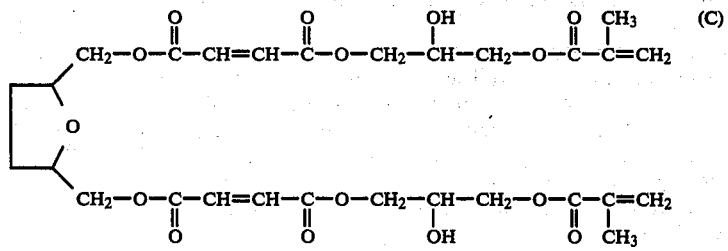

2,5-Dimethyloltetrahydrofuran in the amount of 132 gm (1 mol) and 196 gm (2 mols) of maleic acid anhydride were heated to 100° C. After a reaction time of three hours, the acid number was 352 (calc. 342). This bis-semiester was then reacted with 284 gm (2 mols) of glycidyl methacrylate at 80° C. The reaction was catalyzed by 0.6 gm (0.1%) of benzyltrimethylammonium methoxide. The forming dimethacrylate was stabilized by the addition of 600 mg of hydroquinone. After a reaction time of six hours, the acid number was 12; the reaction was then interrupted. A highly viscous, colorless oil was obtained.

Yield: 612 gm (100% of theor.)
Analysis: $C_{28}H_{36}O_{15}$ (MW 612.60), Calc. C 54.90%, H 5.92%, Found: 54.6%, 5.80%.

EXAMPLE 4

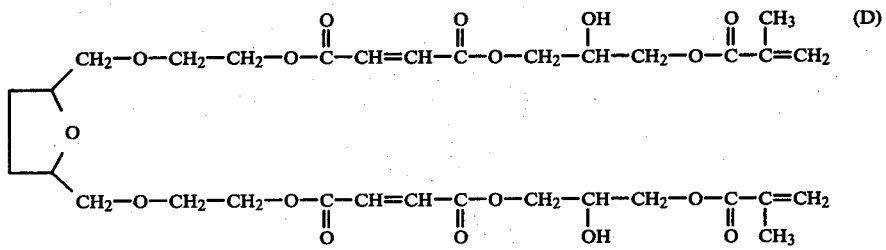

Ethoxylated 2,5-dimethyloltetrahydrofuran (OH number=409.25) in the amount of 165 gm (0.75 mol) was heated to 100° C. with 147 gm (1.5 mol) of maleic acid anhydride. After a reaction time of four hours, the acid number was 287 (calc. 269). The bis-semiester was then reacted with 213 gm (1.5 mol) of glycidyl methacrylate at 80° C., in the presence of 0.5 gm of benzyltrimethylammonium methoxide and 0.5 gm of hydroquinone. After a reaction time of six hours, the acid number was 14. The reaction was interrupted. The resulting oil was highly viscous and colorless.

Yield: 525 gm (100% of theor.)

Analysis: $C_{32}H_{44}O_{17}$ (MW 700.69), Calc. C 54.85%, H 6.33%, Found: 53.8%, 5.83%.

EXAMPLES 5 TO 8

Adhesive Mixtures with the Dimethacrylates

The dimethacrylates of Examples 1 to 4, respectively, were mixed with hydroxyethyl methacrylate at a ratio of 1:1. These monomer mixtures were then mixed with 200 ppm of hydroquinone, 1% of p-toluene sulfonic acid hydrazide, 0.5% of N,N-dimethyl-p-toluidine and 3% of cumene hydroperoxide (70% solution in cumene). The stabilities of all mixtures were above 30 minutes.

In the stability test, a test tube 10 cm long and 10 mm wide was filled 9/10 full with the mixture according to Examples 5 to 8 and suspended in a bath maintained at 80° C. The time from the suspending to the first formation of gel was determined. All samples remained free of gel for more than 30 minutes. These values mean that the products generally are unchanged and stable for more than one year at room temperature.

Comparison Experiment

The dimethacrylate of propoxylated diphenylolpropane (as described in German Published Application No. 22 02 040) was mixed with hydroxyethyl methacrylate at the ratio 1:1. The other additions were the same as in the preceding Examples 5 to 8.

The average torque moment determined for five samples with M 10×30 iron bolts and M 10 nuts as well as the average compressive shear resistance according to DIN outline 54452, of the adhesive bonds obtained with the adhesives of Examples 5 to 8 and the comparison experiment, are compiled in the following Table. The data recorded under the column 150° C. (torque moment) and 180° C. (compressive shear resistance) signify that the samples were heated to 150° C. and 180° C., respectively, for three hours after storing for three days at room temperature, and that the measurement was then taken at this temperature.

TABLE

| Mixture According to Example No. | Torque Moments in Nm | | | Compressive Shear Resistance in N/mm² | |
|---|---|---|---|---|---|
| | 20° C. After 3 Hrs. | 20° C. After 4 Hrs. | 150° C. After 3 Days | 20° C. After 3 Days | 180° C. After 3 Days |
| 5 | 40 | 65 | 24 | 35 | 18 |
| 6 | 30 | 55 | 20 | 30 | 15 |
| 7 | 25 | 68 | 30 | 45 | 20 |
| 8 | 38 | 70 | 32 | 35 | 15 |
| Comparison experiment | 40 | 66 | 14 | 35 | 10 |

These data demonstrate the resistance to heat deterioration of the adhesive bonds of the adhesives produced from the dimethacrylic acid esters of the present invention.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. An adhesive composition hardening under exclusion of oxygen containing from about 10% to about 98.5% by weight of at least one dimethacrylic acid ester of dimethyloltetrahydrofuran and its derivatives having the formula:

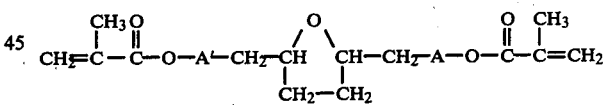

wherein A and A' individually have the formula:

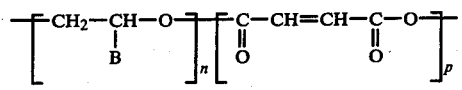

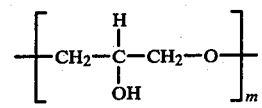

wherein B is a member selected from the group consisting of $CH_3$ and H, n is an integer from 0 to 5, m is 0 or 1, and p is 0 or 1, and the remainder customary ingredients of adhesive compositions hardening under exclusion of oxygen.

2. The adhesive composition of claim 1 wherein said customary ingredients of adhesive compositions includes additional methacrylates.

3. The adhesive composition of claim 2 wherein said additional methacrylates are members selected from the group consisting of difunctional methacrylates and monofunctional methacrylates.

4. The adhesive composition of claim 2 wherein said additional methacrylates are present in an about 1:1 ratio with said at least one dimethacrylic acid ester of dimethyloltetrahydrofuran.

5. The adhesive composition of claim 4 wherein said additional methacrylates are members selected from the group consisting of ethylene glycol dimethacrylate, triethylene glycol dimethacrylate, polyethylene glycol dimethacrylate, hydroxyethyl methacrylate, hydroxypropyl methacrylate, the dimethacrylate of dimethyloltricyclodecane, ethylhexyl methacrylate, cyclohexyl methacrylate, 5,6-dihydrodicyclopentadienyl methacrylate, and tetrahydrofurfuryl methacrylate.

6. The adhesive composition of claim 1 wherein said customary ingredients of adhesive compositions includes from 0.1% to 20% by weight of peroxide initiators.

7. The adhesive composition of claim 6 wherein said peroxide initiators are present in an amount of from 1% to 10% by weight.

8. The adhesive composition of claim 1 wherein said customary ingredients of adhesive compositions includes from 0.1% to 2.5% by weight of at least one organic amine accelerator.

9. The adhesive composition of claim 1 wherein said customary ingredients of adhesive compositions includes from 100 to 1,000 ppm, based on the polymerizable components, of a stabilizer.

10. The adhesive composition of claim 9 wherein said stabilizer is present in an amount of from 200 to 500 ppm.

11. The adhesive composition of claim 1 wherein said customary ingredients of adhesive compositions includes from 0.1% to 20% by weight of plasticizers, thickening agents and pigments in customary adhesive amounts.

* * * * *